(12) United States Patent
Long et al.

(10) Patent No.: US 8,043,272 B2
(45) Date of Patent: Oct. 25, 2011

(54) COLLECTION AND TESTING OF INFANT URINE USING AN ABSORBENT ARTICLE

(75) Inventors: Andrew Long, Appleton, WI (US); Shirlee Ann Weber, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 11/741,929

(22) Filed: Apr. 30, 2007

(65) Prior Publication Data

US 2008/0269706 A1 Oct. 30, 2008

(51) Int. Cl.
*A61F 13/20* (2006.01)
*A61F 13/15* (2006.01)
*A61B 5/00* (2006.01)
*B65D 81/00* (2006.01)
*G01N 1/00* (2006.01)
*G01N 7/00* (2006.01)
*G01F 15/14* (2006.01)
*G01J 5/04* (2006.01)
*G01L 19/14* (2006.01)
*G01P 1/02* (2006.01)

(52) U.S. Cl. ......... 604/385.01; 604/385.14; 604/385.19; 604/385.23; 604/367; 604/369; 604/378; 604/377; 604/374; 600/573; 73/64.56; 73/432.1

(58) Field of Classification Search .................. 604/367, 604/369, 378, 377, 374, 385.01, 385.06, 604/385.14, 385.16, 385.19, 385.23, 395, 604/398; 600/573; 73/64.56, 432.1
See application file for complete search history.

(56) References Cited

U.S. PATENT DOCUMENTS

| 3,731,685 | A | * | 5/1973 | Eidus | 604/361 |
| 3,918,433 | A | * | 11/1975 | Fuisz | 600/573 |
| 4,066,403 | A | * | 1/1978 | Bruschi | 435/12 |
| 4,084,589 | A | | 4/1978 | Kulvi | |
| 4,507,121 | A | * | 3/1985 | Leung | 604/361 |
| 4,637,979 | A | | 1/1987 | Skjold et al. | |
| 4,657,855 | A | | 4/1987 | Corey et al. | |
| 4,700,714 | A | | 10/1987 | Fuisz | |
| 4,704,116 | A | | 11/1987 | Enloe | |
| 4,778,459 | A | * | 10/1988 | Fuisz | 604/378 |
| 4,798,603 | A | | 1/1989 | Meyer et al. | |

(Continued)

FOREIGN PATENT DOCUMENTS

GB 2163656 A 3/1986

(Continued)

OTHER PUBLICATIONS

Patent Abstract of JP3210193 of Kawanishi, Sep. 1991.

*Primary Examiner* — Leslie Deak
*Assistant Examiner* — Adam Marcetich
(74) *Attorney, Agent, or Firm* — Dority & Manning, P.A.

(57) ABSTRACT

A collection insert for use in a diaper for the testing of the urine of a baby is generally disclosed. The collection insert is configured to collect and temporarily retain the urine, allowing the urine to be later tested for the presence of absence of an analyte. The collection insert is fluidly isolated from the absorbent core of the diaper, and can be positioned between the bodyside liner and the outer cover or located in a pocket defined by the bodyside liner. The collection insert can include an insert cover and a collection core, such as a sponge, cellulosic material, polymeric nonwoven material, and the like. Additionally, the collection insert can be substantially free of superabsorbent material.

20 Claims, 6 Drawing Sheets

U.S. PATENT DOCUMENTS

| | | | |
|---|---|---|---|
| 4,804,377 A | 2/1989 | Hanifl et al. | |
| 4,806,423 A | 2/1989 | Hugl et al. | |
| 4,814,271 A | 3/1989 | Hugl et al. | |
| 5,075,077 A | 12/1991 | Durley, III et al. | |
| 5,192,606 A | 3/1993 | Proxmire et al. | |
| 5,252,459 A | 10/1993 | Tarcha et al. | |
| 5,354,289 A * | 10/1994 | Mitchell et al. | 604/361 |
| 5,383,867 A * | 1/1995 | Klinger | 604/385.23 |
| 5,399,219 A | 3/1995 | Roessler et al. | |
| 5,405,342 A * | 4/1995 | Roessler et al. | 604/364 |
| 5,464,739 A | 11/1995 | Johnson et al. | |
| 5,486,166 A | 1/1996 | Bishop et al. | |
| 5,490,846 A | 2/1996 | Ellis et al. | |
| 5,540,796 A | 7/1996 | Fries | |
| 5,569,229 A * | 10/1996 | Rogers | 604/385.09 |
| 5,595,618 A | 1/1997 | Fries et al. | |
| 5,613,959 A | 3/1997 | Roessler et al. | |
| 5,663,044 A | 9/1997 | Noffsinger et al. | |
| 5,670,381 A | 9/1997 | Jou et al. | |
| 5,702,377 A | 12/1997 | Collier, IV et al. | |
| 5,750,359 A | 5/1998 | Huh et al. | |
| 5,810,799 A * | 9/1998 | Slater | 604/385.09 |
| 5,876,389 A * | 3/1999 | Bouchard et al. | 604/385.16 |
| 5,902,296 A * | 5/1999 | Fluyeras | 604/361 |
| 5,931,823 A | 8/1999 | Stokes et al. | |
| 5,968,028 A | 10/1999 | Roe et al. | |
| 6,060,638 A | 5/2000 | Paul et al. | |
| 6,090,090 A | 7/2000 | Roe et al. | |
| 6,149,590 A * | 11/2000 | Smith et al. | 600/367 |
| 6,150,002 A | 11/2000 | Varona | |
| 6,213,992 B1 * | 4/2001 | Dreier | 604/385.01 |
| 6,375,643 B1 | 4/2002 | Moorhead et al. | |
| 6,551,292 B1 | 4/2003 | D'Acchioli et al. | |
| 6,579,273 B2 | 6/2003 | Dupuy | |
| 6,689,935 B2 | 2/2004 | Chen et al. | |
| 6,719,691 B2 * | 4/2004 | Kritzman et al. | 600/362 |
| 6,932,800 B2 * | 8/2005 | LaVon et al. | 604/385.14 |
| 6,951,552 B2 | 10/2005 | D'Acchioli et al. | |
| 6,989,005 B1 | 1/2006 | LaVon et al. | |
| 7,175,613 B2 * | 2/2007 | Sugiyama et al. | 604/385.14 |
| 7,387,620 B2 * | 6/2008 | Watanabe et al. | 604/385.14 |
| 2002/0007161 A1 * | 1/2002 | Bouchard et al. | 604/354 |
| 2002/0165515 A1 * | 11/2002 | Burnham | 604/385.14 |
| 2003/0023188 A1 * | 1/2003 | Kritzman et al. | 600/575 |
| 2003/0124739 A1 | 7/2003 | Song et al. | |
| 2003/0199844 A1 * | 10/2003 | LaVon et al. | 604/385.14 |
| 2004/0039361 A1 * | 2/2004 | LaVon et al. | 604/385.01 |
| 2004/0102750 A1 | 5/2004 | Jameson | |
| 2004/0220538 A1 | 11/2004 | Panopoulos | |
| 2005/0054255 A1 | 3/2005 | Morman et al. | |
| 2005/0059941 A1 | 3/2005 | Baldwin et al. | |
| 2006/0069362 A1 | 3/2006 | Odorzynski et al. | |
| 2006/0286616 A1 * | 12/2006 | Furukawa et al. | 435/7.92 |
| 2007/0021728 A1 * | 1/2007 | Speak | 604/395 |
| 2007/0078420 A1 * | 4/2007 | Sugiyama et al. | 604/361 |
| 2007/0185466 A1 * | 8/2007 | Co | 604/349 |

FOREIGN PATENT DOCUMENTS

| | | |
|---|---|---|
| JP | 3210193 | 9/1991 |
| WO | WO 9516425 | 6/1995 |
| WO | WO 0049948 A2 | 8/2000 |
| WO | WO 2006020074 | 2/2006 |

* cited by examiner

COLLECTION AND TESTING OF INFANT URINE USING AN ABSORBENT ARTICLE

BACKGROUND

The collection and testing of urine samples is a frequent need in the care of newborn babies, especially premature babies. However, due to the fragile nature of newborn and premature babies' skin, caregivers must exercise care in collecting the urine samples. As a current practice, caregivers typically collect urine samples by bagging the child, or at least the lower torso of the child, within a collection bag. Then, once the child urinates, the urine is held within the bag. The caregiver can then collect the bag containing the urine sample, and wash the baby's skin.

However, the baby sitting in a puddle of urine and excessive washing of babies' skin can lead to skin irritation, rash, and other skin-related problems. Thus, a need exists for an improved collection and testing method for newborn and premature babies that can help minimize skin-related issues arising from collection bags.

SUMMARY

In general, a diaper for collecting and temporarily retaining urine from a baby is generally provided. The diaper includes an absorbent core positioned between a bodyside liner and an outer cover. A collection insert is posited in the crotch region of the diaper, and is configured to collect and temporarily retain urine. For example, the collection insert can be positioned between the bodyside liner and the outer cover, or can be located in a pocket defined by the bodyside liner. The collection insert is fluidly isolated from the absorbent core. The bodyside liner can define a slot configured to allow the insertion of a dip stick through the bodyside liner and into the collection insert.

In one embodiment, the collection insert includes an insert cover and a collection core. The collection core can be a sponge, cellulosic material, polymeric nonwoven material, and the like. Additionally, the collection insert can be substantially free of superabsorbent material.

In another embodiment, a method of testing for the presence or absence of an analyte in urine is generally provided. According to the method, a diaper having an absorbent core positioned between a bodyside liner and an outer cover is provided. The diaper includes a collection insert fluidly isolated from the absorbent core and configured to collect and temporarily retain urine. The urine collected by the collection insert is tested for the presence or absence of an analyte.

In another method, the urine of a newborn or premature baby can be tested for the presence or absence of an analyte. This method includes first providing a diaper having an absorbent core positioned between a bodyside liner and an outer cover. The diaper has a collection insert fluidly isolated from the absorbent core and configured to collect and temporarily retain urine. The diaper is placed adjacent the baby so that the collection insert is positioned to collect urine discharged from the baby. Then, the urine collected by the collection insert can be tested for the presence or absence of an analyte.

Other features and aspects of the present invention are described in more detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
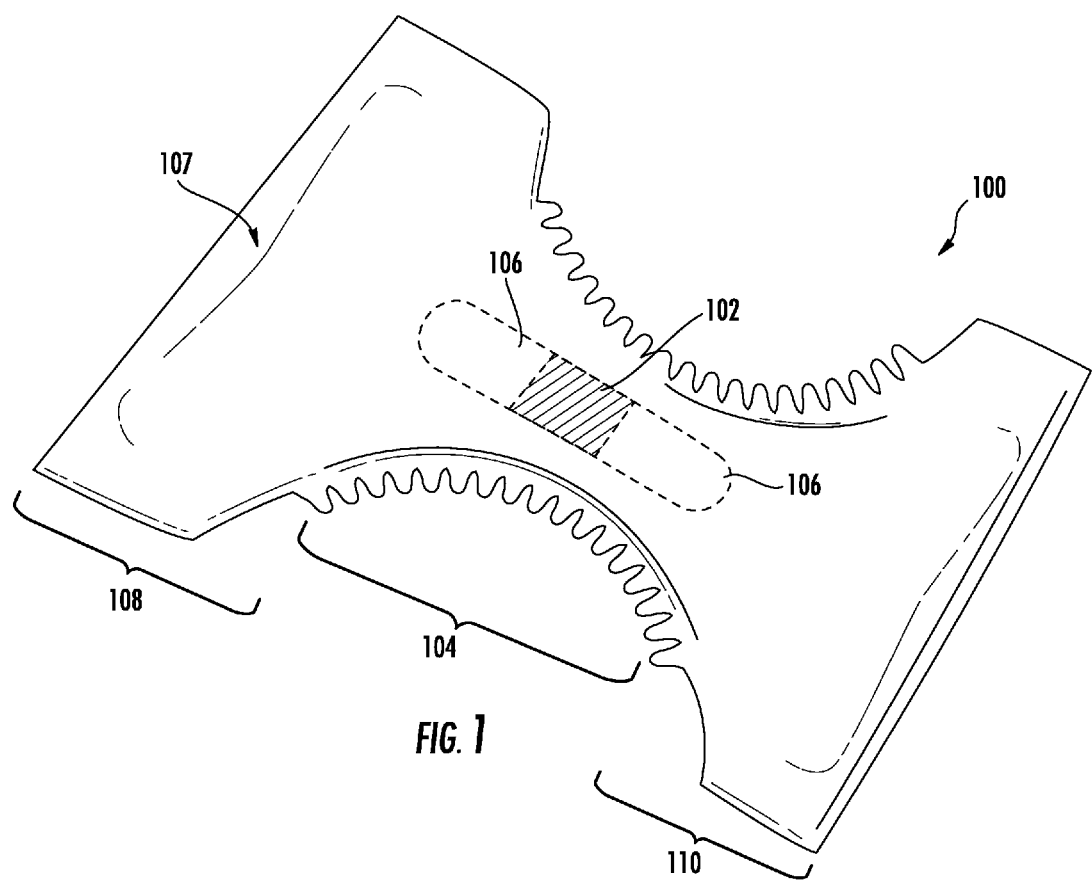
FIG. 1 is a perspective view of an exemplary embodiment of an collection insert shown in a diaper.

Repeat use of reference characters in the present specification and drawings is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

Generally speaking, the present invention is directed to the collection and testing of urine samples from babies, particularly newborn and premature babies (i.e., babies weighing less than about 15 pounds). In some embodiments, the urine samples can be simultaneously collected and tested for the presence or absence of an analyte. As one advantage of the present invention, urine from a newborn or premature baby can be collected and tested with in a more convenient and healthy manner than bagging the baby. For example, the articles and methods of the present invention can help protect the skin of the baby from excess contact with urine and other bodily fluids. Thus, excess washing of the baby can be avoided, helping to maintain the skin's health.

Accordingly, an absorbent article having a collection insert located within the target zone (e.g., the crotch region) is generally provided. The collection insert can be integral with the absorbent article, or can be removably inserted into or attached to the absorbent article. No matter its construction, the collection insert is configured to collect and retain a sufficient amount of urine in order to enable testing, while still allowing the majority of the urine to be trapped in the absorbent core of the absorbent article.

I. Collection Insert

As stated, the collection insert of the present invention is configured to retain a sufficient amount of urine for testing. However, the collection insert can still enable the absorbent core of the diaper to absorb any excess urine, allowing the diaper to adequately wick urine away from the skin of the wearer and inhibit leaks into the surrounding environment. In some embodiments, the absorbent core of the diaper absorbs a majority (i.e., more than 50% by weight) of the urine released into the diaper. As such, the collection insert collects only the desired amount of the urine discharged into the diaper.

Figure 3:
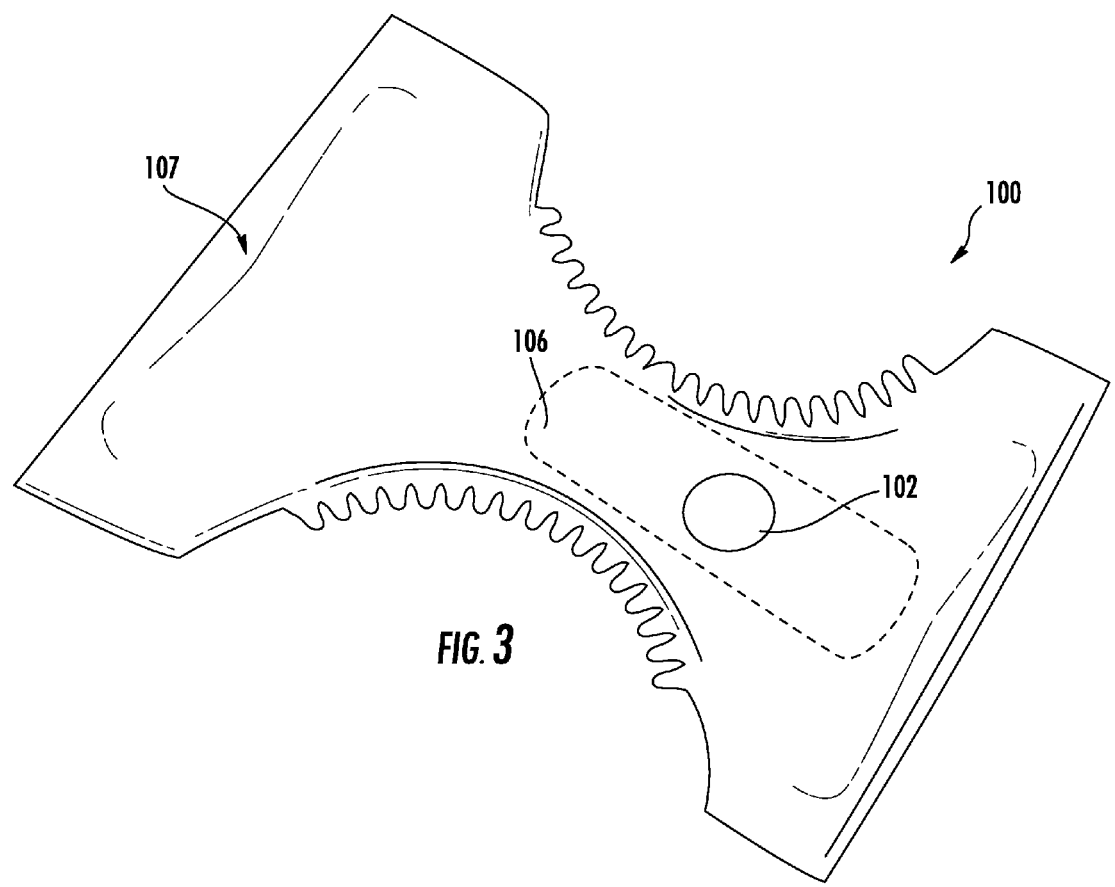
FIG. 3 is a perspective view of an exemplary embodiment of an collection insert shown in a diaper.

The collection insert is generally located in the target zone of the diaper where urine is expected to be discharged. For example, referring to FIG. 1, a diaper 100 including a collection insert 102 is generally shown in the middle portion of the crotch region 104 (e.g., generally in the middle of the length and width of the diaper). The collection insert 102 is shown surrounded in the front and back by absorbent core material 106. As shown, the collection insert 102 and absorbent cores 106 are located within the construction of the diaper 100. Specifically, the collection insert 102 and the absorbent cores 106 are positioned between the bodyside liner 107 and outer cover 109. As shown in FIG. 3, the collection insert 102 can be completely surrounded by the absorbent core 106.

Figure 2:
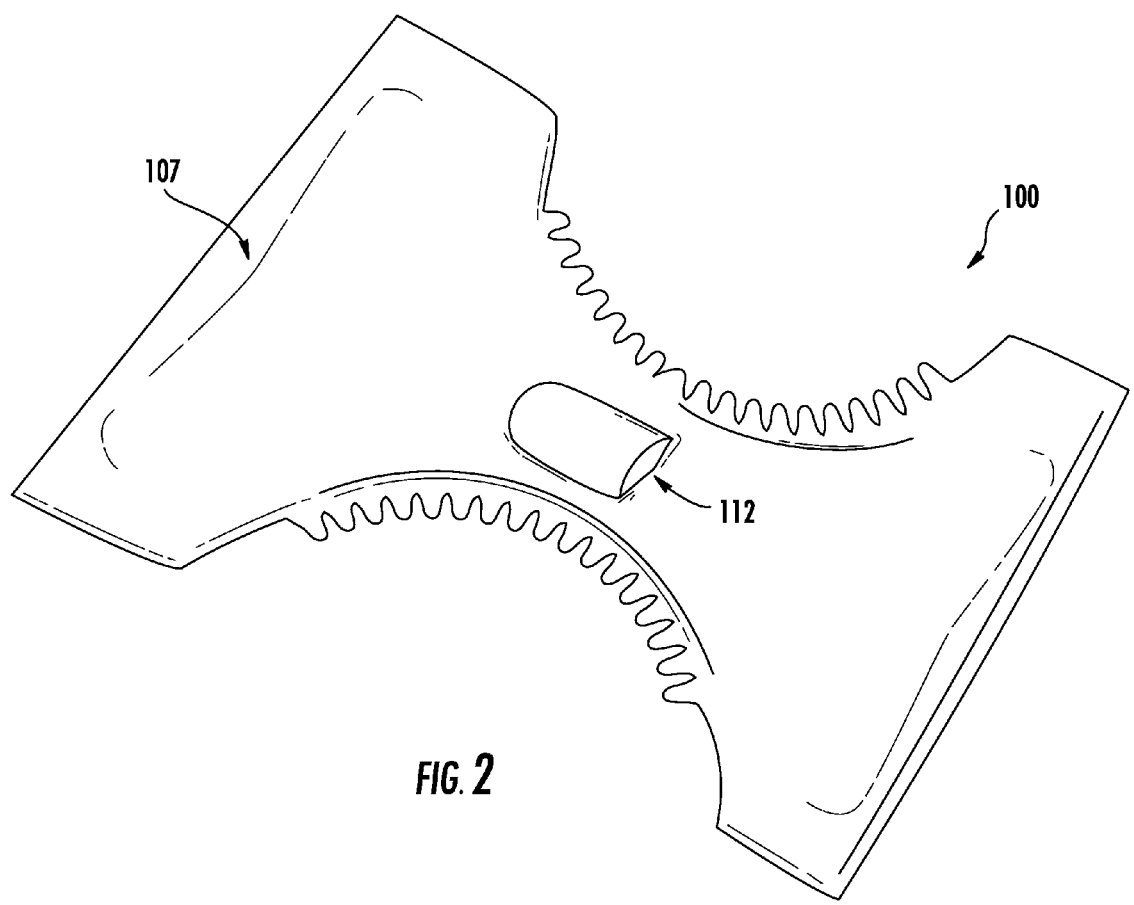
FIG. 2 is a perspective view of an exemplary embodiment of a diaper for use with an collection insert.

However, in alternative embodiments, the collection insert 102 may be positioned on the outer surface of the bodyside liner 107. For example, as shown in FIG. 2, the collection insert 102 can be posited within a pocket 112 located in the target zone and positioned on the bodyside liner 107. Thus, the collection insert 102 is releaseably attached to the diaper 100 and can be removed when desired. Once removed from the pocket 112, the urine contained in the collection insert can be released for testing in any manner. Additionally, the collection insert can be attached to the bodyside liner 107 in another manner. For example, the collection insert can be adhesively attached to the bodyside liner. Likewise, the collection insert can be attached to the bodyside liner via a hook and loop-type attachment mechanism.

Generally, the collection insert include any material suitable to collect and temporarily retain urine for later testing. However, if the collection insert includes material that is configured to more permanently retain urine, such as super-absorbent material, then the collected urine may not be readily available for testing. Additionally, the collection insert preferably does not alter the urine composition. Materials such as superabsorbent polymers and absorbent hydrogel materials may not allow any urine be released once absorbed. Thus, in one particular embodiment, the collection insert is substantially free from superabsorbent material and/or absorbent hydrogel materials (e.g., less than 1% by weight). As such, the collection insert can be super-absorbent free and/or absorbent hydrogel material free, allowing the collected urine to be readily released for testing when desired.

In one embodiment, collection insert includes a compressed sponge. Upon wetting, the compressed sponge swells to retain the urine within the sponge. Thus, when it is desired to release the collected urine from the sponge, the sponge can be re-compressed (e.g., squeezed), which causes the collected urine to be released from the sponge. The sponge can include any suitable material, such as natural sponge, regenerated cellulose sponge materials, etc. Densified cross-linked cellulosic mats can also be used for the collection insert, as can crosslinked cellulosic fibers in general.

Of course, the collection insert is not limited to compressed sponges. In fact, any absorbent material which is generally conformable, non-irritating to the wearer's skin and capable of collecting and temporarily retaining liquids may be utilized in the construction of the collection insert. For instance, the collection insert can be constructed of comminuted wood pulp, creped cellulose wadding, absorbent foams, polymeric fibers, or any equivalent materials or combinations of materials. In one embodiment, for instance, the collection insert includes a meltblown tissue of one or more layers. Each layer can have a basis weight of about 30 grams to about 100 grams per square meter (gsm) and made in accordance with U.S. Pat. No. 4,798,603 issued to Meyer and assigned to Kimberly-Clark Corporation, the entire disclosure of which is incorporated herein by reference and made a part hereof.

The collection insert can include cellulosic fluff from a blend of wood pulp fluff. One preferred type of fluff is identified with the trade designation CR 1654, available from U.S. Alliance of Childersburg, Ala., USA, and is a bleached, highly absorbent wood pulp containing primarily soft wood fibers. The absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. Methods and apparatus for carrying out such techniques are well known in the art.

The total absorbent capacity of the collection insert should, however, be compatible with the desired urine sample size for testing. Further, the size of the collection insert may be varied to accommodate a predetermined desired amount of fluid volume. For instance, a different absorbent capacity may be utilized for collection inserts intended for high volume testing, when compared to the collection insert intended for use with dip-stick testing devices. In most embodiments, the total absorbency of the collection insert can be less than about 100 grams of saline solution (0.9 weight %), such as from about 1 gram to about 75 grams. Typically, the total absorbency of the collection insert can be less than about 50 g of saline, such as from about 1 gram to about 25 grams. Furthermore, when testing with a device requiring a small sample size, such as a dip-stick device, the absorbent capacity of the collection insert can be from about 1 gram to about 10 grams.

Additionally, the collection insert may be utilized in a wide variety of sizes and shapes of absorbent articles, such as rectangular, circular, hourglass or racetrack to name a few. After being formed or cut into a desired shape, the collection insert may be wrapped or encompassed by a suitable wrap that aids in maintaining the integrity and shape of the collection insert. As such, the collection insert can include a collection core encased within an insert cover.

In one embodiment, the insert cover can serve to inhibit wicking of the collected urine from the collection core to the absorbent core of the diaper. Since the absorbent core of the diaper is more hydrophilic (e.g., typically contains superabsorbent materials), the urine is susceptible to wicking out of the collection core and into the absorbent core without any barrier or other preventative mechanism. Thus, the insert cover can be constructed of a liquid impermeable material to inhibit the passage of urine from the insert to the absorbent core of the diaper. The collection insert can, in one embodiment, be fluidly isolated (e.g., not in fluid communication) from the absorbent core.

As such, the collection insert can be completely encased within a liquid impermeable sheet to prevent the passage of urine out of the collection insert. However, in this embodiment, the insert cover can be provided with apertures located on the top portion (i.e., the bodyside liner facing) in order to allow urine to enter the collection insert upon wetting of the diaper.

Alternatively, the collection core can be wrapped with a liquid impermeable sheet only about those areas that contact the absorbent core material. As such, the collection insert can be encased with a liquid impermeable sheet about its side edges and bottom portion, leaving the top portion contacting the bodyside liner uncovered, or covered with a liquid permeable material. Thus, urine can readily flow into the collection insert, but is substantially prevented from wicking out of the collection insert and into the absorbent core.

The liquid impermeable sheets that can encase the collection insert may be formed from a thin plastic film or other flexible liquid-impermeable material. In one embodiment, liquid impermeable sheet is formed from a polyethylene film. However, other material may be used. For instance, those liquid impermeable sheets discussed below in reference to the outer cover of a diaper may be used as the collection insert cover.

II. Absorbent Article

In accordance with the present invention, the collection insert can be inserted into or attached onto any absorbent article designed for infants, including newborn and premature babies. Typically, absorbent articles include a substantially liquid-impermeable layer (e.g., outer cover), a liquid-permeable layer (e.g., bodyside liner, surge layer, etc.), and an absorbent core.

Various embodiments of an absorbent article that may be formed according to the present invention will now be described in more detail. For purposes of illustration only, an absorbent article is shown in FIG. 1 as a diaper 100. In the illustrated embodiment, the diaper 100 is shown as having an hourglass shape in an unfastened configuration. However, other shapes may of course be utilized, such as a generally rectangular shape, T-shape, or I-shape. The diaper 100 includes a chassis formed by various components, generally including an absorbent core positioned between an outer cover 109 and a bodyside liner 107. It should be understood, however, that other layers may also be used in exemplary embodiments of the present invention. For example, a surge layer may be present in the construction of the absorbent article, such as those surge layers described in U.S. Pat. No. 5,486,166 to Ellis et al. and U.S. Pat. No. 5,490,846 to Ellis et al., which are incorporated herein in their entirety by reference thereto for all purposes. Likewise, one or more of the layers referred to in FIG. 1 may also be eliminated in certain exemplary embodiments of the present invention.

The bodyside liner 107 is generally employed to help isolate the wearer's skin from liquids held in the absorbent core. For example, the liner 107 presents a bodyfacing surface that is typically compliant, soft feeling, and non-irritating to the wearer's skin. Typically, the liner 107 is also less hydrophilic than the absorbent core so that its surface remains relatively dry to the wearer. As indicated above, the liner 107 may be liquid-permeable to permit liquid to readily penetrate through its thickness. Exemplary liner constructions that contain a nonwoven web are described in U.S. Pat. Nos. 5,192,606 to Proxmire, et al.; 5,702,377 to Collier, IV, et al.; 5,931,823 to Stokes, et al.; 6,060,638 to Paul, et al.; and 6,150,002 to Varona, as well as U.S. Patent Application Publication Nos. 2004/0102750 to Jameson; 2005/0054255 to Morman, et al.; and 2005/0059941 to Baldwin, et al., all of which are incorporated herein in their entirety by reference thereto for all purposes.

The outer cover 109 is typically formed from a material that is substantially impermeable to liquids. For example, the outer cover 109 may be formed from a thin plastic film or other flexible liquid-impermeable material. In one embodiment, the outer cover 109 is formed from a polyethylene film having a thickness of from about 0.01 millimeter to about 0.05 millimeter. The film may be impermeable to liquids, but permeable to gases and water vapor (i.e., "breathable"). This permits vapors to escape from the absorbent core 103, but still prevents liquid exudates from passing through the outer cover 109. If a more cloth-like feeling is desired, the outer cover 109 may be formed from a polyolefin film laminated to a nonwoven web. For example, a stretch-thinned polypropylene film may be thermally laminated to a spunbond web of polypropylene fibers.

In some embodiments, the diaper 100 may also include a pair of side panels (or ears) (not shown) that extend from the side edges of the diaper 100 into one of the waist regions. The side panels may be integrally formed with a selected diaper component. For example, the side panels may be integrally formed with the outer cover 109 or from the material employed to provide the top surface. In alternative configurations, the side panels may be provided by members connected and assembled to the outer cover 109, the top surface, between the outer cover 109 and top surface, or in various other configurations. If desired, the side panels may be elasticized or otherwise rendered elastomeric by use of the elastic nonwoven composite of the present invention. Examples of absorbent articles that include elasticized side panels and selectively configured fastener tabs are described in PCT Patent Application WO 95/16425 to Roessler; U.S. Pat. No. 5,399,219 to Roessler et al.; U.S. Pat. No. 5,540,796 to Fries; and U.S. Pat. No. 5,595,618 to Fries, each of which is incorporated herein in its entirety by reference thereto for all purposes.

The diaper 100 may also include a pair of containment flaps that are configured to provide a barrier and to contain the lateral flow of body exudates. The containment flaps may be located along the laterally opposed side edges of the bodyside liner 107 adjacent the side edges of the absorbent core. The containment flaps may extend longitudinally along the entire length of the absorbent core, or may only extend partially along the length of the absorbent core. When the containment flaps are shorter in length than the absorbent core, they may be selectively positioned anywhere along the side edges of diaper 100 in a crotch region 104. In one embodiment, the containment flaps extend along the entire length of the absorbent core to better contain the body exudates. Such containment flaps are generally well known to those skilled in the art. For example, suitable constructions and arrangements for the containment flaps are described in U.S. Pat. No. 4,704,116 to Enloe, which is incorporated herein in its entirety by reference thereto for all purposes.

To provide improved fit and to help reduce leakage of body exudates, the diaper 100 may be elasticized with suitable elastic members, as further explained below. For example, as representatively illustrated in FIG. 1, the diaper 100 may include leg elastics constructed to operably tension the side margins of the diaper 100 to provide elasticized leg bands which can closely fit around the legs of the wearer to reduce leakage and provide improved comfort and appearance. Waist elastics may also be employed to elasticize the end margins of the diaper 100 to provide elasticized waistbands. The waist elastics are configured to provide a resilient, comfortably close fit around the waist of the wearer.

The diaper 100 may also include one or more fasteners. For example, two flexible fasteners can be on opposite side edges of waist regions to create a waist opening and a pair of leg openings about the wearer. The shape of the fasteners may generally vary, but may include, for instance, generally rectangular shapes, square shapes, circular shapes, triangular shapes, oval shapes, linear shapes, and so forth. The fasteners may include, for instance, a hook-and-loop material, buttons, pins, snaps, adhesive tape fasteners, cohesives, fabric-and-loop fasteners, etc. In one particular embodiment, each fastener includes a separate piece of hook material affixed to the inside surface of a flexible backing.

However, in one particular embodiment, a diaper for newborn and/or premature babies can be specially constructed for collecting urine for testing. Newborn and premature babies generally weigh less than 15 lbs, with some premature babies weighing much less (e.g., about 2 to about 6 pounds). These newborn and premature babies are typically immobile and do not even roll over when placed on their backs. Due to this immobility, the need for a fastened diaper is significantly reduced. Thus, in one embodiment, the diaper can be configured to wrap around the buttocks, through the crotch, and rest gently on the genital area of the baby, without any fastening mechanism in use. In fact, the diaper can be constructed without a fastening mechanism.

Figure 6:
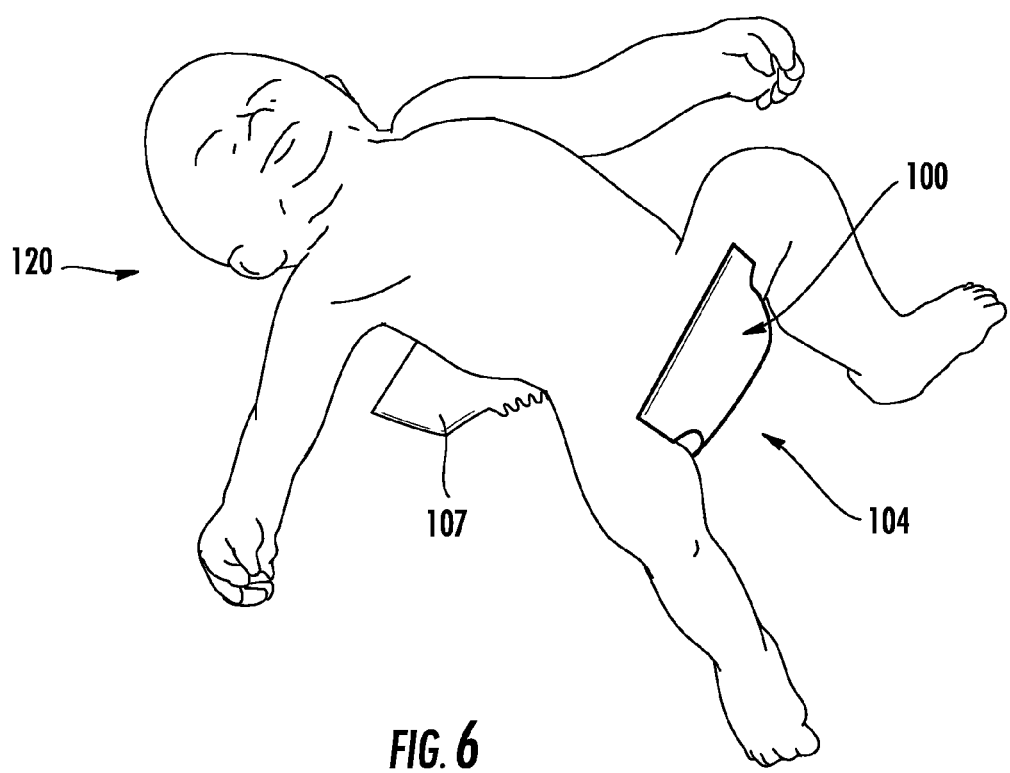
FIG. 6 is a perspective view of an exemplary diaper of the present invention worn by a newborn or premature baby.

In this configuration, the collection insert can be positioned adjacent to the genitals of the baby, allowing the collection insert to collect any urine discharged by the baby. For example, referring to FIG. 6, a baby 120 is shown laying on its back with a diaper 100 wrapped between its crotch region 104 without any fastening mechanism included on the diaper 100. Thus, a caregiver can easily lift the front portion of the diaper 100 to expose the collection insert 102 for testing or removal, without having to change the diaper.

The various regions and/or components of the diaper 100 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In the illustrated embodiment, for example, the outer cover 109 and bodyside liner 107 are assembled to each other and to the absorbent core using an adhesive. Alternatively, the absorbent core may be connected to the outer cover 109 using conventional fasteners, such as buttons, hook and loop type fasteners, adhesive tape fasteners, and so forth. Similarly, other diaper components, such as the leg elastic members 106, waist elastic members 108 and fasteners, may also be assembled into the diaper 100 using any attachment mechanism.

III. Sample Testing

Generally speaking, any testing method can be utilized to test the urine sample collected in the insert. For instance, the caregiver can extract and preserve the urine collected by the collection insert into a sample suitable for any desired test. However, in some embodiments, the urine can be tested without the need to extract the urine from the collection insert.

Figure 4:
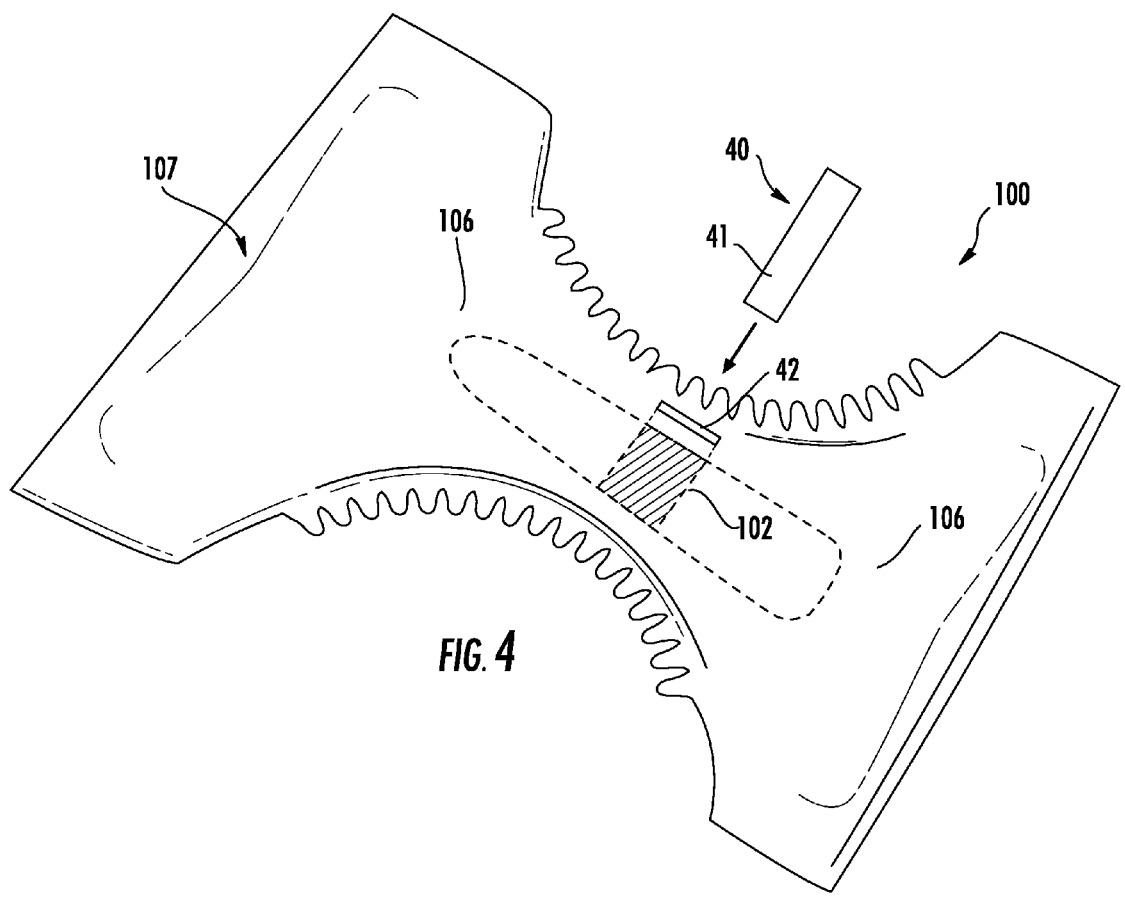
FIG. 4 is a perspective view of an exemplary embodiment of testing fluid in an collection insert of a diaper.

In one embodiment, the urine sample within the collection insert can be tested by a dip-stick device without removing the collection insert from the absorbent article. Typically, only one end of the dip-stick devices needs to contact the urine sample to initiate testing of the sample. For instance, referring to FIG. 4, the sample testing end 41 of dip stick 40 is inserted into slot 42 located in the bodyside liner 107. Slot 42 leads to contact with the collection insert 102 in diaper 100. As such, the dip stick 40 can contact urine retained within the collection insert 102 to initiate testing of the urine. The slot 42 can be positioned anywhere on the bodyside liner 102 for enabling contact of the dip stick 40 with the collection insert 102. Additionally, the slot 42 can be sized so that the dip stick 40 snugly fits within the slot. Thus, release of urine from the slot is prevented upon the dip stick entering and compressing the collection insert.

Any suitable dip-stick device can be utilized according to the present invention. Such dip-stick testing devices are commonly known in the art for testing urine samples for the presence or absence of an analyte. In one particular embodiment, the dip-stick device can be a lateral flow assay device that performs a heterogeneous assay. A heterogeneous assay is one in which a species is separated from another species prior to detection. Separation may be carried out by physical separation, e.g., by transferring one of the species to another reaction vessel, filtration, centrifugation, chromatography, solid phase capture, magnetic separation, and so forth. The separation may also be nonphysical in that no transfer of one or both of the species is conducted, but the species are separated from one another in situ. In some embodiments, for example, a heterogeneous immunoassay is performed that utilizes mechanisms of the immune systems, wherein antibodies are produced in response to the presence of antigens that are pathogenic or foreign to the organisms. These antibodies and antigens, i.e., immunoreactants, are capable of binding with one another, thereby causing a highly specific reaction mechanism that may be used to determine the presence or concentration of that particular antigen in a fluid test sample. In other embodiments, however, the heterogeneous assay may employ non-specific chemical reactions to achieve the desired separation.

Figure 5:
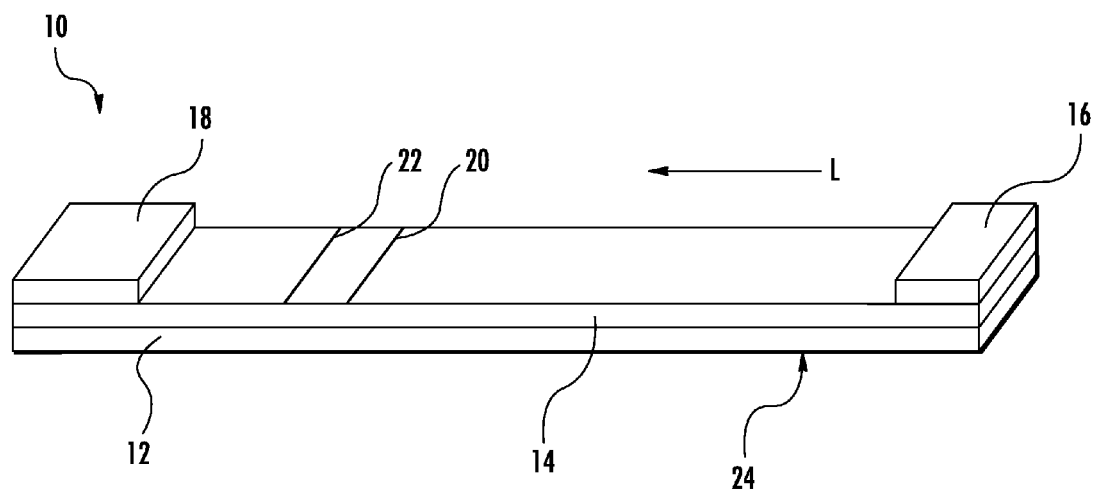
FIG. 5 is a perspective view of an exemplary lateral flow device that could be used to test the bodily fluid.

In any event, the use of a lateral flow assay device provides a variety of benefits, including a more uniform flow of the bodily fluid and reagents during testing. This may enhance the accuracy of the test and minimize the need for external control mechanisms. Referring to FIG. 5, for example, one embodiment of a lateral flow assay device 10 will now be described in more detail. As shown, the device 10 contains a chromatographic medium 14 optionally supported by a rigid support 12. The chromatographic medium 14 may be made from any of a variety of materials through which the test sample is capable of passing. For example, the chromatographic medium 14 may be a porous membrane formed from synthetic or naturally occurring materials, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth. In one particular embodiment, the chromatographic medium 14 is formed from nitrocellulose and/or polyether sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The size and shape of the chromatographic medium 14 may generally vary as is readily recognized by those skilled in the art. For instance, a porous membrane strip may have a length of from about 10 to about 100 millimeters, in some embodiments from about 20 to about 80 millimeters, and in some embodiments, from about 40 to about 60 millimeters. The width of the membrane strip may also range from about 0.5 to about 20 millimeters, in some embodiments from about 1 to about 15 millimeters, and in some embodiments, from about 2 to about 10 millimeters. Likewise, the thickness of the membrane strip is generally small enough to allow transmission-based detection. For example, the membrane strip may have a thickness less than about 500 micrometers, in some embodiments less than about 250 micrometers, and in some embodiments, less than about 150 micrometers.

As stated above, the support 12 carries the chromatographic medium 14. For example, the support 12 may be positioned directly adjacent to the chromatographic medium 14 as shown in FIG. 5, or one or more intervening layers may be positioned between the chromatographic medium 14 and the support 12. Regardless, the support 12 may generally be formed from any material able to carry the chromatographic medium 14. The support 12 may be formed from a material that is transmissive to light, such as transparent or optically diffuse (e.g., translucent) materials. Also, it is generally desired that the support 12 is liquid-impermeable so that fluid flowing through the medium 14 does not leak through the support 12. Examples of suitable materials for the support include, but are not limited to, glass; polymeric materials, such as polystyrene, polypropylene, polyester (e.g., Mylar® film), polybutadiene, polyvinylchloride, polyamide, polycarbonate, epoxides, methacrylates, and polymelamine; and so forth. To provide a sufficient structural backing for the chromatographic medium 14, the support 12 is generally selected to have a certain minimum thickness. Likewise, the thickness of the support 12 is typically not so large as to adversely affect its optical properties. Thus, for example, the support 12 may have a thickness that ranges from about 100 to about 5,000 micrometers, in some embodiments from about 150 to about 2,000 micrometers, and in some embodiments, from about 250 to about 1,000 micrometers. For instance, one suitable membrane strip having a thickness of about 125 micrometers may be obtained from Millipore Corp. of Bedford, Mass. under the name "SHF180UB25."

The chromatographic medium 14 may be cast onto the support 12, wherein the resulting laminate may be die-cut to the desired size and shape. Alternatively, the chromatographic medium 14 may simply be laminated to the support 12 with, for example, an adhesive. In some embodiments, a nitrocellulose or nylon porous membrane is adhered to a Mylar® film. An adhesive is used to bind the porous membrane to the Mylar® film, such as a pressure-sensitive adhesive. Laminate structures of this type are believed to be commercially available from Millipore Corp. of Bedford, Mass. Still other examples of suitable laminate device structures are described in U.S. Pat. No. 5,075,077 to Durley. III, et al., which is incorporated herein in its entirety by reference thereto for all purposes.

The device 10 may also contain an absorbent material 18 that is positioned adjacent to the medium 14. The absorbent material 18 can help promote capillary action and fluid flow through the medium 14. In addition, the absorbent material 18 receives fluid that has migrated through the entire chromatographic medium 14 and thus draws any unreacted components away from the detection region to help reduce the likelihood of "false positives." Some suitable absorbent materials that may be used in the present invention include, but are not limited to, nitrocellulose, cellulosic materials, porous polyethylene pads, glass fiber filter paper, and so forth. The absorbent material may be wet or dry prior to being incorporated into the device. Pre-wetting may facilitate capillary flow for some fluids, but is not typically required. Also, as is well known in the art, the absorbent material may be treated with a surfactant to assist the wicking process.

To initiate the detection of an analyte, the bodily fluid (e.g., urine) may be applied to a portion of the chromatographic medium 14 through which it may then travel in the direction illustrated by arrow "L" in FIG. 5. Alternatively, the fluid may first contact a sample application zone 16 that is in fluid communication with the chromatographic medium 14. The sample application zone 16 may be defined by a separate pad or material as shown in FIG. 5, or simply defined by the chromatographic medium 14. In the illustrated embodiment, the fluid may travel from the sample application zone 16 to a conjugate pad (not shown) that is placed in communication with one end of the sample pad. The conjugate pad may contain one or more diffusively immobilized reagents, and be formed from a material through which a fluid is capable of passing (e.g., glass fibers). Some suitable materials that may be used to form the absorbent material 18 and/or sample pad include, but are not limited to, nitrocellulose, cellulose, porous polyethylene pads, and glass fiber filter paper. If desired, the sample pad may also contain one or more assay pretreatment reagents, either diffusively or non-diffusively attached thereto.

Regardless of the particular manner in which it is formed, the lateral flow assay device of the present invention employs one or more zones for providing an indicator of the presence of an analyte. More specifically, such zone(s) typically contain a chemical or biological reagent that interacts with the analyte and/or other reagents to generate a signal (e.g., visual signal). Referring again to FIG. 5, for example, the lateral flow assay device 10 includes a detection zone 20 within which a capture reagent is disposed. Typically, the capture reagent is applied in a manner so that it does not substantially diffuse through the matrix of the chromatographic medium 14 (i.e., non-diffusively immobilized). This enables a user to readily detect the change in color that occurs upon reaction of the capture reagent with other compounds. The capture reagent may, for example, form an ionic and/or covalent bond with functional groups present on the surface of the chromatographic medium 14 so that it remains immobilized thereon. For instance, particles, such as described below, may facilitate the immobilization of the reagent at the detection zone 20. Namely, the reagent may be coated onto particles, which are then immobilized on the chromatographic medium 14 of the device 10. In this manner, the reagent is able to readily contact compounds flowing through the medium 14.

Another zone that may be employed in the lateral flow assay device 10 for improving detection accuracy is a control zone 22. The control zone 22 gives a signal to the user that the test is performing properly. More specifically, reagents may be employed that flow through the chromatographic medium 14 upon contact with a sufficient volume of the bodily fluid being tested. These reagents may then be observed, either visually or with an instrument, within the control zone 22. The control reagents generally contain a detectable substance, such as luminescent compounds (e.g., fluorescent, phosphorescent, etc.); radioactive compounds; visual compounds (e.g., colored dye or metallic substance, such as gold); liposomes or other vesicles containing signal-producing substances; enzymes and/or substrates, and so forth. Other suitable detectable substances may be described in U.S. Pat. Nos. 5,670,381 to Jou, et al. and 5,252,459 to Tarcha et al., which are incorporated herein in their entirety by reference thereto for all purposes.

If desired, one or more of the reagents employed in the assay device may be disposed on particles (sometimes referred to as "beads" or "microbeads"). Among other things, the particles enhance the ability of the reagent to travel through a chromatographic medium. For instance, naturally occurring particles, such as nuclei, mycoplasma, plasmids, plastids, mammalian cells (e.g., erythrocyte ghosts), unicellular microorganisms (e.g., bacteria), polysaccharides (e.g., agarose), etc., may be used. Further, synthetic particles may also be utilized. For example, in one embodiment, latex microparticles that are labeled with a fluorescent or colored dye are utilized. Although any synthetic particle may be used in the present invention, the particles are typically formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. When utilized, the shape of the particles may generally vary. In one particular embodiment, for instance, the particles are spherical in shape. However, it should be understood that other shapes are also contemplated by the present invention, such as plates, rods, discs, bars, tubes, irregular shapes, etc. In addition, the size of the particles may also vary. For instance, the average size (e.g., diameter) of the particles may range from about 0.1 nanometers to about 1,000 microns, in some embodiments, from about 0.1 nanometers to about 100 microns, and in some embodiments, from about 1 nanometer to about 10 microns. Commercially available examples of suitable particles include fluorescent carboxylated microspheres sold by Molecular Probes, Inc. under the trade names "FluoSphere" (Red 580/605) and "Transfluo-Sphere" (543/620), as well as "Texas Red" and 5- and 6-carboxytetramethylrhodamine, which are also sold by Molecular Probes, Inc.

In addition, commercially available examples of suitable colored, latex microparticles include carboxylated latex beads sold by Bang's Laboratory, Inc.

The location of the detection zone 20 and control zone 22 may vary based on the nature of the test being performed. In the illustrated embodiment, for example, the control zone 22 is defined by the chromatographic medium 14 and positioned downstream from the detection zone 20. In such embodiments, the control zone 22 may contain a material that is non-diffusively immobilized in the manner described above and forms a chemical and/or physical bond with the control reagents. When the control reagents contain latex particles, for instance, the control zone 22 may include a polyelectrolyte that binds to the particles. Various polyelectrolytic binding systems are described, for instance, in U.S. Patent App. Publication No. 2003/0124739 to Song, et al., which is incorporated herein in it entirety by reference thereto for all purposes. In alternative embodiments, however, the control zone 22 may simply be defined by a region of the absorbent material 18 to which the control reagents flow after traversing through the chromatographic medium 14.

Regardless of the particular control technique selected, the application of a sufficient volume of the test sample to the device 10 will cause a signal to form within the control zone 22, whether or not the enzyme or other analyte of interest is present. Among the benefits provided by such a control zone is that the user or other personnel are informed that a sufficient volume of test sample has been added without requiring careful measurement or calculation. This provides the ability to use the lateral flow assay device 10 without the need for externally controlling the reaction time, test sample volume, etc. In the case of the elderly, children, or patients unable to communicate clearly, control zone 22 provides an indication that a sample was discharged, collected, and successfully tested.

The detection zone 20, control zone 22, or any other zone employed in the lateral flow assay device 10 may generally provide any number of distinct detection regions so that a user may better determine the concentration of the enzyme or other analyte within the test sample. Each region may contain the same or different materials. For example, the zones may include two or more distinct regions (e.g., lines, dots, etc.). The regions may be disposed in the form of lines in a direction that is substantially perpendicular to the flow of the test sample through the device 10. Likewise, in some embodiments, the regions may be disposed in the form of lines in a direction that is substantially parallel to the flow of the test sample through the device 10.

The specific reagents employed in the lateral flow assay device depend on the analyte of interest and the assay technique employed. In one particular embodiment, for example, it may be desirable to detect the presence of leukocytes in urine as an early diagnosis of urinary tract infection ("UTI"). Although leukocytes are normally present in the urine, it has been determined that the threshold limit for pathological levels is about $1 \times 10^4$ leukocytes per milliliter of uncentrifuged urine. When leukocytes are present in urine, leukocyte esterase is produced and may be used as a biomarker for the presence of leukocytes.

A variety of reagents may be used for detecting the presence of the leukocyte esterase enzyme. One such reagent is a substrate that is chemically acted upon or "cleaved" by the enzyme of interest to release a product. For example, the substrate may be an ester that is catalytically hydrolyzed in the presence of leukocyte esterase to yield an aromatic compound. The aromatic esters may include, for instance, indoxyl esters having the following general formula:

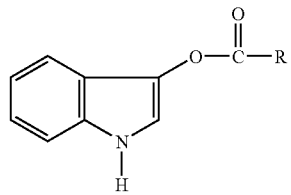

wherein, R may be substituted or unsubstituted, and may be an alkyl group, an alkyoxy group, a hydroxyalkyl group, an alkylene group, a fatty acid group, and so forth. In addition, the aromatic rings may also be substituted or unsubstituted. Specific examples include, for instance, indoxyl acetate, indoxyl butyrate, indoxyl laureate, indoxyl stearate, indoxyl ester of a N-blocked amino acid or peptide and thioindoxyl analogs thereof, and N-Tosyl-L-alanine 3-indoxyl ester. Such indoxyl esters are hydrolyzed by the leukocyte esterase to form a benzopyrrole, such as indoxyl, which has the following structure:

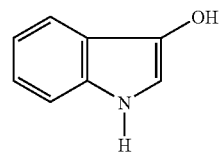

Lactate esters may also be used, such as described in U.S. Pat. Nos. 5,464,739 to Johnson, et al. and 5,663,044 to Noffsinger, et al., which are incorporated herein in their entirety by reference thereto for all purposes. Lactate esters are generally hydrolyzed by the leukocyte esterase to provide a hydroxy-pyrrole compound. Other suitable ester substrates include thiazole esters, pyrrole esters, thiophene esters, naphthyl esters, phenoxyl esters, quinolinyl esters, such as described in U.S. Pat. Nos. 5,750,359 to Huh et al.; 4,657,855 to Corey, et al.; and Japanese Publication No. 03210193 to Kawanishi, et al., which are incorporated herein in their entirety by reference thereto for all purposes.

Typically, the substrate is diffusively immobilized on the lateral flow assay device 10 prior to application of the urine or other bodily fluid. The substrate is preferably disposed downstream from the sample application zone 16. In this manner, the test sample is capable of mixing with the enzyme upon application. If desired, the pH may be maintained at a relatively neutral level to facilitate the desired enzyme-catalyzed reaction, such as described above. To accomplish the desired pH level, a buffer may be mixed with the substrate prior to application to the device 10. Alternatively, the buffer may be separately applied to the lateral flow assay device 10 so that it is capable of mixing with the reagents upon exposure the bodily fluid being tested.

Regardless, an aromatic compound is released through cleavage of the substrate that is capable of inducing a color change in the presence of certain reagents. The released aromatic compound is a nucleophile in that it contains a group that is electron rich (e.g., amine) and that may form bonds with electron deficient groups. For example, indoxyl esters are hydrolyzed by the leukocyte esterase to form indoxyl. Indoxyl contains an electron-rich, aromatic ring system that is capable of undergoing electrophilic attack by a diazonium ion having the generic formula:

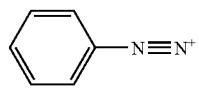

The diazonium ion may be zwitterionic in that the counterion of the diazonium moiety is covalently bound to the ring system. The ring system of the diazonium ion may be substituted or unsubstituted. The ion may be provided by a variety of suitable diazonium salts, such as diazonium chlorides, diazonium acid sulphates, diazonium alkyl sulphates, diazonium fluoborates, diazonium benzenesulphonates, diazonium acid 1,5-naphthalenedisulphonates, and so forth. Specific examples of diazonium salts are 1-diazo-2-naphthol-4-sulfonate; 1-diazophenyl-3-carbonate; 4-diazo-3-hydroxy-1-naphthylsulfonate (DNSA); 4-diazo-3-hydroxy-7-nitro-1-naphthylsulfonate (NDNSA); 4-diazo-3-hydroxy-1,7-naphthyldisulfonate; 2-methoxy-4-(N-morpholinyl) benzene diazonium chloride; 4-diazo-3-hydroxy-7-bromo-1-naphthylsulfonate; and 4-diazo-3-hydroxy-7-[1,oxopropyl]-1-naphthylsulfonate. One particularly desired diazonium salt is 5-chloro-2-methoxybenzenediazonium chloride, which has a yellow color and is classified under the name "Diazo Red RC" or "Fast Red RC." More specifically, "Fast Red RC" has the following structure:

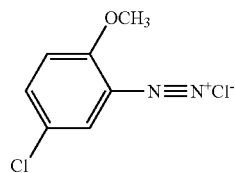

Other suitable diazonium salts are classified by the common names "Fast Red B" and "Fast Blue B." Still other suitable diazonium salts may be described in U.S. Pat. Nos. 4,637,979 to Skjold, et al.; 4,806,423 to Hugh, et al.; and 4,814,271 to Hugl, et al., which are incorporated herein in their entirety by reference thereto for all purposes.

As indicated above, the nucleophilic aromatic compounds released by the hydrolysis of the substrate are capable of undergoing electrophilic attack by a reagent (e.g., diazonium ion). This reaction is often referred to as "coupling" and results in the formation of another reagent having a different color. For example, diazonium ions may react with aromatic compounds to form an aromatic azo compound having the generic formula, R—N=N—R', wherein "R" and "R'" are aryl groups. Without intending to be limited by theory, it is believed that this reaction induces either a shift of the absorption maxima towards the red end of the spectrum ("bathochromic shift") or towards the blue end of the spectrum ("hypsochromic shift"). The type of absorption shift depends on the nature of the resulting azo molecule and whether it functions as an electron acceptor (oxidizing agent), in which a hypsochromic shift results, or whether it functions as an electron donor (reducing agent), in which a bathochromic shift results. The absorption shift provides a color difference that is detectable, either visually or through instrumentation, to indicate the presence of leukocyte esterase or other enzymes within the test sample. For example, prior to contact with an infected test sample, the diazonium ion may be colorless or it may possess a certain color. However, after contacting the test sample and reacting with an aromatic compound released by hydrolysis of the substrate, an aromatic azo compound will form that exhibits a color that is different than the initial color of the diazonium ion. Exemplary aromatic azo compounds that may be formed include dimethyldiazene, diphenydiazene, 1-naphthyl-2-naphthyl diazene, 3-chlorophenyl-4-chlorophenyl diazene, methylvinyl diazene, and 2-naphthylphenyl diazene. In one particular embodiment, for instance, "Fast Red RC" (yellow), a diazonium ion, may react with indoxyl to form an aromatic azo compound that is red and has the following general structure (may be substituted or unsubstituted):

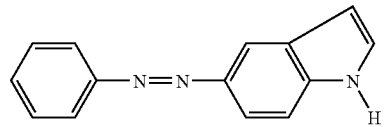

Normally, the above-described diazonium ion is immobilized within the detection zone 20 of the lateral flow assay device 10. The diazonium ion may be applied directly to the medium 14 or first formed into a solution prior to application. Various solvents may be utilized to form the solution, such as, but not limited to, acetonitrile, dimethylsulfoxide (DMSO), ethyl alcohol, dimethylformamide (DMF), and other polar organic solvents. For instance, the amount of a diazonium salt in the solution may range from about 0.001 to about 100 milligrams per milliliter of solvent, and in some embodiments, from about 0.1 to about 10 milligrams per milliliter of solvent. In one particular embodiment, the detection zone 20 is defined by the chromatographic medium 14 and formed by coating a solution thereon using well-known techniques and then dried. The diazonium ion concentration may be selectively controlled to provide the desired level of detection sensitivity.

Typically, the diazonium ion is applied in a manner so that it does not substantially diffuse through the matrix of the chromatographic medium 14 (i.e., non-diffusively immobilized), which enables a user to readily detect the change in color that occurs upon reaction of the diazonium ion with a nucleophilic aromatic compound. The diazonium ion may form an ionic and/or covalent bond with functional groups present on the surface of the chromatographic medium 14 so that it remains immobilized thereon. For instance, particles, such as described below, may facilitate the immobilization of the diazonium ion at the detection zone 20. Namely, the diazonium ion may be coated onto particles, which are then immobilized on the chromatographic medium 14 of the device 10. In this manner, the diazonium ion is able to readily contact nucleophilic aromatic compounds flowing through the medium 14.

One benefit of the lateral flow assay device is its ability to readily incorporate one or more additional reagent zones to facilitate the desired reactions. By way of example, a reagent zone (not shown) may be utilized. In the illustrated embodiment, the reagent zone may be located such that test sample travels from the sample application zone 16 to a reagent zone that is in fluid communication with the sample application zone 16. The reagent zone may be formed on the medium 14. Alternatively, the reagent zone may be formed from a separate material or pad. Such a reagent pad may be formed from any material through which the test sample is capable of passing, such as glass fibers.

In addition to the zones specified above, the lateral flow assay device 10 may also include other optional zones. For example, the lateral flow assay device 10 may include an accelerator zone (not shown) in which is contained an accelerator for the enzyme-catalyzed substrate reaction. Typically, the accelerator is diffusively immobilized within the accelerator zone in the manner described above so that it may flow through the medium 14 upon contact with the test sample. The location of the accelerator zone may generally vary, so long as it positioned upstream from the detection zone 20. For example, in some embodiments, the accelerator zone may be positioned at a location (e.g., sample application zone 16) that is upstream from the application of the substrate (e.g., reagent zone). Due to the separation provided between the substrate and accelerator, the likelihood of any premature reaction therebetween is thus reduced. It should be understood, however, that the accelerator may nevertheless be combined with the substrate in some applications.

Another zone that may be employed is a quenching zone (not shown). The quenching zone is configured to remove compounds from the test sample that would otherwise interfere with the accuracy of the detection system. For example, contaminants within the test sample (e.g., phenolics, bilirubin, urobilinogen, etc.) may react with the diazonium ion within the detection zone 20 and form an aromatic azo compound, thereby producing a "false negative" result. Thus, the quenching zone may contain a quenching agent, such as a diazonium ion, that is capable of reacting with the reaction contaminants. The quenching agent may be the same or different than the detection agent used within the detection zone 20. Typically, the quenching agent is non-diffusively immobilized within the quenching zone in the manner described above so that it does not flow through the medium 14 and interfere with testing. The location of the quenching zone may vary, but is typically positioned upstream from the detection zone 20 and the location at which the substrate is applied to avoid interference with enzyme detection. For example, in the illustrated embodiment, the quenching zone may be positioned immediately downstream of the sample application zone 16 and over medium 14. Alternatively, the quenching zone may be positioned upstream from the sample application zone 16.

An exemplary method for detecting the presence of leukocyte esterase within a test sample using the device 10 of FIG. 5 will now be described in more detail. Initially, urine containing leukocyte esterase is discharged to the sample application zone 16 and travels in the direction "L" to a reagent zone. At the reagent zone, the esterase is able to mix with and begin to initiate the catalytic reaction. While flowing through the medium, the enzyme and substrate react to release an aromatic product that subsequently couples with a diazonium ion to form a colored aromatic azo compound in the detection zone 20. After the reaction, the detection zone 20 changes color, which may be indicative of urinary tract infection. Due to the nature of the controlled fluid flow, any unreacted substrate travels to the end of the reaction medium so that it is unable to adversely interfere with observance of the aromatic azo compound in the detection region.

Of course, the present invention is by no means limited to the diagnosis of urinary tract infection. Numerous health conditions may be diagnosed through testing of bodily fluids such as urine. Testing for even a single condition may require that multiple different analytes be targeted. By way of example, the assay device may employ specific binding pairs to test for the presence of certain biological analytes (e.g., antibodies, antigens, etc.). Specific binding members generally refer to a member of a specific binding pair, i.e., two different molecules where one of the molecules chemically and/or physically binds to the second molecule. For instance, immunoreactive specific binding members may include antigens, haptens, aptamers, antibodies (primary or secondary), and complexes thereof, including those formed by recombinant DNA methods or peptide synthesis. An antibody may be a monoclonal or polyclonal antibody, a recombinant protein or a mixture(s) or fragment(s) thereof, as well as a mixture of an antibody and other specific binding members. The details of the preparation of such antibodies and their suitability for use as specific binding members are well known to those skilled in the art. Other common specific binding pairs include but are not limited to, biotin and avidin (or derivatives thereof), biotin and streptavidin, carbohydrates and lectins, complementary nucleotide sequences (including probe and capture nucleic acid sequences used in DNA hybridization assays to detect a target nucleic acid sequence), complementary peptide sequences including those formed by recombinant methods, effector and receptor molecules, hormone and hormone binding protein, enzyme cofactors and enzymes, enzyme inhibitors and enzymes, and so forth. Furthermore, specific binding pairs may include members that are analogs of the original specific binding member. For example, a derivative or fragment of the analyte, i.e., an analyte-analog, may be used so long as it has at least one epitope in common with the analyte.

Still other analytes of interest may include proteins, enzymes, nitrites, ketones, various bacteria, red or white blood cells, glucose, bilirubin, urobilinogen, and so forth. By way of example, the presence of nitrites in urine may indicate a urinary tract infection or even other bacterial infections in the body. To test for the presence of nitrites, the assay device may, for example, employ a substrate diffusively immobilized on the chromatographic medium that includes both an aromatic amine and another aromatic compound. The amine is selected so that it will react with the nitrite to form a diazonium salt. The salt, in turn, may react with the aromatic compound to generate an azo dye that provides a visual indication, by a color change, that nitrite has been detected.

IV. Kits and Methods

In another embodiment, a kit for testing the urine of a baby is generally provided. The kit can include both the testing device and an absorbent article. The absorbent article and the testing device can include any of the configurations or modifications described above. As such, any number of combinations of testing devices and absorbent articles can be utilized within the kit.

In yet another embodiment, a method for detecting the presence or absence of an analyte in the urine of a baby is generally disclosed. The method can include testing the urine collected by a collection insert in conjunction with an absorbent article, as described above. Then, the collected urine can be tested according to any method, including the use of a testing device. As such, any of a variety of different combinations of testing devices and absorbent articles with collection inserts can be used within the method.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A diaper defining a crotch region for collecting and temporarily retaining urine from a baby, the diaper comprising:
a liquid permeable bodyside liner, wherein the bodyside liner defines a pocket in the crotch region;
a liquid impermeable outer cover;
an absorbent core positioned between the bodyside liner and the outer cover;
a collection insert positioned within the pocket and comprising a collection core encased by a liquid impermeable sheet, wherein the collection insert is configured to collect and temporarily retain urine, and wherein the collection insert is removably attached to the diaper, the liquid impermeable sheet positioned between the collection core and the absorbent core to prevent passage of urine out of the collection core and into the absorbent core such that the collection core is fluidly isolated from the absorbent core, and wherein apertures are located on a top portion of the liquid impermeable sheet facing the bodyside liner to allow urine to enter the collection core upon wetting of the diaper.

2. A diaper as in claim 1, wherein the collection insert is positioned between the bodyside liner and the outer cover.

3. A diaper as in claim 1, wherein the collection core comprises a sponge.

4. A diaper as in claim 1, wherein the collection core comprises a cellulosic material.

5. A diaper as in claim 1, wherein the collection insert is substantially free of superabsorbent material.

6. A diaper as in claim 1, wherein the bodyside liner defines a slot configured to allow the insertion of a dip stick through the bodyside liner and into the collection insert.

7. A diaper as in claim 1, wherein the diaper is without a fastening mechanism.

8. The diaper of claim 1, wherein the outer cover, the absorbent core, and the bodyside liner are assembled to each other using an adhesive.

9. A method of testing for the presence or absence of an analyte in urine, the method comprising
removing a collection insert from a diaper having an absorbent core positioned between a bodyside liner and an outer cover, wherein the collection insert is configured to collect and temporarily retain urine and comprises a collection core encased by a liquid impermeable sheet such that the liquid impermeable sheet is positioned between the collection insert and the absorbent core to prevent passage of urine out of the collection insert and into the absorbent core such that the collection insert is fluidly isolated from the absorbent core, wherein the collection insert is removably attached to the diaper, and wherein apertures are located on a top portion facing the bodyside liner in order to allow urine to enter the collection core upon wetting of the diaper; and
testing the urine collected by the collection insert for the presence or absence of an analyte.

10. A method as in claim 9 further comprising inserting the collection insert into a pocket defined by the bodyside liner.

11. A method as in claim 10, wherein the step of testing the urine comprises removing the collection insert from the pocket and extracting the urine from the collection insert.

12. A method as in claim 9, wherein the step of testing the urine comprises contacting a dip stick with the urine collected by the collection insert.

13. A method as in claim 12, wherein the dip stick is a lateral flow device.

14. A method as in claim 9, wherein the collection core comprises a sponge.

15. A method as in claim 9, wherein the collection core comprises a cellulosic material.

16. A method as in claim 9, wherein the collection insert is substantially free of superabsorbent material.

17. The method of claim 9, wherein the outer cover, the absorbent core, and the bodyside liner are assembled to each other using an adhesive.

18. A method of testing urine of a newborn or premature baby for the presence or absence of an analyte, the method comprising:
placing a diaper adjacent the baby so that a collection insert is positioned to collect urine discharged from the baby, wherein the diaper has an absorbent core positioned between a bodyside liner and an outer cover, wherein the diaper includes the collection insert in a pocket formed by the bodyside liner, wherein the collection insert comprises a collection core encased by a liquid impermeable sheet to prevent passage of urine out of the collection insert and into the absorbent core such that the collection insert is fluidly isolated from the absorbent core, wherein apertures are located on a top portion of the liquid impermeable sheet facing the bodyside liner to allow urine to enter the collection core upon wetting of the diaper, and wherein the collection insert is removably attached to the diaper;
removing the collection insert from the diaper; and
testing the urine collected by the collection insert for the presence or absence of an analyte.

19. A method as in claim 18, wherein the collection insert is substantially free of superabsorbent material.

20. The method of claim 18, wherein the outer cover, the absorbent core, and the bodyside liner are assembled to each other using an adhesive.

* * * * *